United States Patent [19]

Slater et al.

[11] Patent Number: 5,359,993
[45] Date of Patent: Nov. 1, 1994

[54] APPARATUS FOR COUNTING THE NUMBER OF TIMES A MEDICAL INSTRUMENT HAS BEEN USED

[75] Inventors: Charles R. Slater, Fort Lauderdale; Thomas O. Bales, Miami; Jurgen A. Kortenbach, Miami Springs; George Nunez; David Turkel, both of Miami, all of Fla.

[73] Assignee: Symbiosis Corporation, Miami, Fla.

[21] Appl. No.: 998,951

[22] Filed: Dec. 31, 1992

[51] Int. Cl.$^5$ .......................... A61B 1/00; G01K 5/00
[52] U.S. Cl. ....................... 128/4; 606/205; 116/216; 116/221; 235/139 A
[58] Field of Search ............... 116/206, 207, 216, 284, 116/221; 235/131 JA, 139 A, 142, 144 ME; 128/4; 606/205

[56] References Cited

U.S. PATENT DOCUMENTS

| | | | |
|---|---|---|---|
| 4,382,063 | 5/1983 | Romito et al. | 116/207 X |
| 5,143,453 | 9/1992 | Weynant nee Girones | 116/221 |
| 5,174,300 | 12/1992 | Bales et al. | 606/205 X |

Primary Examiner—Richard J. Apley
Assistant Examiner—Beverly A. Meindl
Attorney, Agent, or Firm—David P. Gordon

[57] ABSTRACT

An apparatus for counting the number of times a medical instrument has been sterilized includes an indicator having sequential indicia and a heat responsive member for indicating a next one of the indicia. Mechanical, fluid mechanical and electronic versions of the invention are disclosed. In the mechanical version, the indicator can be a ratchet member having teeth, a pawl and a display surface containing indicia. A heat responsive element such as a bimetallic member engages the teeth of the ratchet and advances the ratchet each time the apparatus is subjected to the heat of sterilization. A housing with a window masks the display to indicate one of the indicia as advanced by the heat responsive element. Preferred embodiments of the mechanical version include a ring-like ratchet member with interior teeth and an exterior display surface. The number of teeth is preferably one or more less than the number of indicia so that upon advancing the ratchet member to the last indicia, it can be advanced no further. The bimetallic element is mounted inside the ring and the housing covers the outer surface of the ring. The housing may be formed from the ferrule of an endoscopic surgical instrument or may be formed as part of the handle of such an instrument. A removable locking pin is provided to prevent movement of the ratchet member during shipping and the locking pin may be coupled to packaging so that it is automatically removed when the surgical instrument is removed from its packaging.

55 Claims, 12 Drawing Sheets

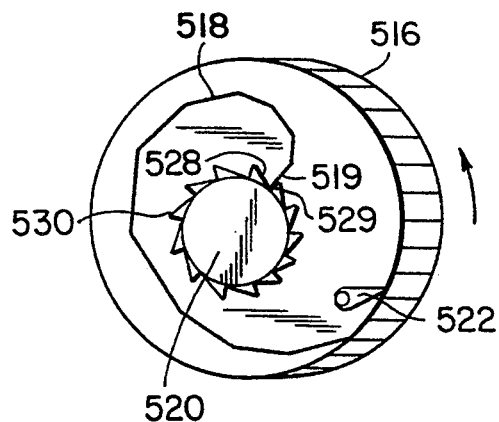
FIG. 5
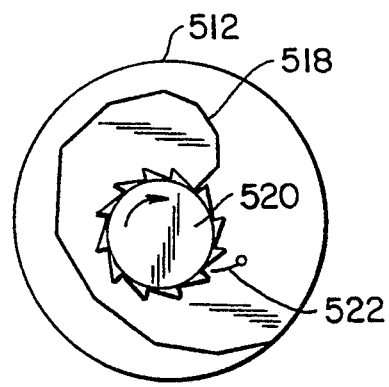
FIG. 5a
FIG. 5b
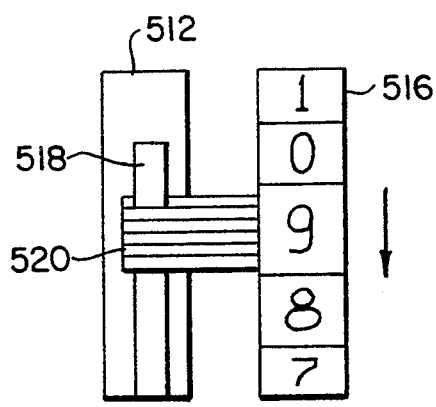
FIG. 6
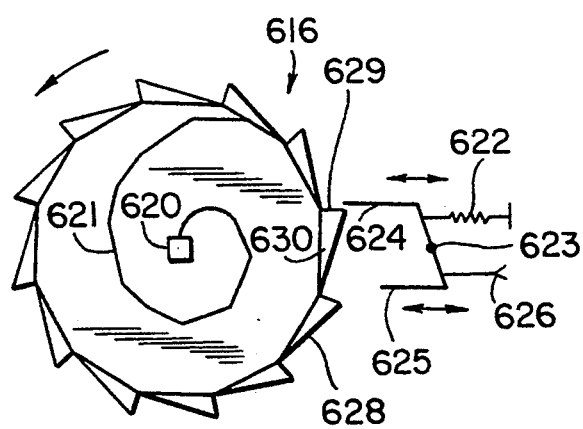
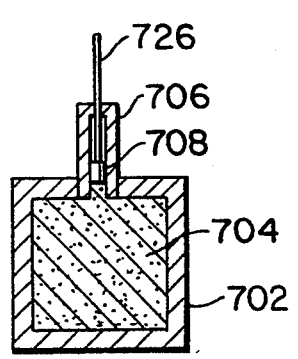
FIG. 7

APPARATUS FOR COUNTING THE NUMBER OF TIMES A MEDICAL INSTRUMENT HAS BEEN USED

BACKGROUND OF THE INVENTION

This invention relates to medical instruments. More particularly, this invention relates to an apparatus for automatically counting the number of times a medical or surgical instrument has been sterilized. The invention finds particular use in endoscopic surgical instruments which should be disposed of after a certain number of uses.

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera or magnifying lens is often inserted through the largest diameter trocar tube (e.g. 10 mm diameter), while a cutter, dissector, or other surgical instrument is inserted through a smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the camera in place in the larger trocar tube.

By 1996, it is expected that more than two million additional endosurgeries will be performed per year that, in 1990, were done via open surgery (MedPRO Month, I:12, p.178). The advantages of endoscopic surgery are clear in that it is less invasive, less traumatic and recovery is typically quicker. As a result, many new instruments and devices for use in endosurgery are introduced every year. Most endoscopic instruments have similar configurations with a proximal handle, an actuation mechanism, and distal end effectors coupled by a tube through which the actuation mechanism extends. The end effectors take many forms such as grippers, cutters, forceps, dissectors and the like. Some endoscopic instruments are provided with a ferrule on the tube so that the tube which carries the end effectors can be rotated relative to the handle. Initially, endoscopic surgical instruments were very expensive, partly because they must be very small but still durable and reliable and the materials necessary to provide these features are expensive.

Recently, a number of "disposable" endoscopic instruments have been introduced and their use is now widely accepted. One of the advantages of disposable endoscopic instruments over reusable instruments is that because they are used only a single time, there are no sterilization problems, and no concerns about the dulling or nicking of blades or wearing of parts. However, in order to justify disposing of instruments after a single use, the instruments have to be much less expensive than the reusable tools. In order to manufacture the instruments less expensively, the disposable instruments therefore use less expensive materials. As a result, the disposable instruments are less durable than the reusable instruments, which is not of concern where the instruments are used only once. However, in order to reduce the costs of medical procedures, many hospitals and surgeons have recently started to sterilize and reuse the "disposable" endoscopic instruments. This practice can be problematic. While the disposable endoscopic instruments typically are not so fragile that they must be disposed of after a single use, clearly, they may not be used as many times as the typical stainless steel reusable instruments as they are more likely to malfunction and dull after several uses. Presently, there is no scientific mechanism available for determining how many times a medical instrument has been used, and the surgeon or the surgical staff must devise their own system to keep track of the number of times a tool has been used so that it will not be used after its useful life has expired.

SUMMARY OF THE INVENTION

It is therefore an object of the invention to provide an automatic mechanism for tracking the number of times a surgical instrument has been used.

It is also an object of the invention to provide a counter mechanism which is integral with a surgical instrument so that the instrument itself will display the number of times it has been used or the number of times it may still be used with confidence.

It is another object of the invention to provide a use counter for surgical instruments which is activated by the sterilization process.

It is a further object of the invention to provide a mechanism by which a use counter for surgical instruments will not be erroneously triggered before an initial use of the surgical instrument.

It is yet another object of the invention to provide a use counter for surgical instruments which will count up to a preset number and not repeat.

A further object of the invention to provide use counters for endoscopic surgical instruments which may be located in either the handle section of the instrument or a more distal portion of the instrument.

The instant invention is premised upon the concept that the number of uses of a surgical instrument may be counted by counting the number of times the instrument has been sterilized. The sterilization of medical devices is usually accomplished by one of two standard methods: autoclaving at a temperature of typically 220°-250° F., or ETO (ethylene oxide gas sterilization) at a temperature of typically 140°-150° F.

In accord with the aforestated objects of the invention, the surgical instrument use counter broadly comprises a use indicator attached to the surgical instrument where the indicator has a predetermined plurality of sequential indicia, and heat responsive means for indicating a next one of the indicia when the surgical instrument is sterilized. Typically, the surgical instrument is provided with a display window and at least a portion of the heat responsive means is viewable through the display window. Also, the use indicator typically incrementally advances each time the surgical instrument is subjected to sterilization. Preferably the advancing of the use indicator occurs as the surgical instrument cools, although advancement may occur during heating. The preferred heat responsive means mechanism is a curved bimetallic pawl which expands and contracts with changes in temperature, although other mechanical, chemical, electrical, or combination mechanisms may be utilized. By arranging the use indicator as a ratchet member with a plurality of teeth and an outside display surface, the curved bimetallic pawl or other heat responsive means can expand over a ratchet tooth as the instrument and bimetallic pawl are heated, and then catch behind the tooth and advance the ratchet as the instrument and bimetallic pawl cool. Alternatively, the curved bimetallic pawl or other heat responsive means can be arranged so that it expands behind the tooth and advances the ratchet as the instrument and bimetallic pawl are heated, and then contracts over a ratchet tooth as the instrument and bimetallic pawl cool. As the ratchet is advanced, the outside display surface of the ratchet moves past the window in the instrument and displays a new use indication or incremental number. To prevent backward movement of the ratchet member, a second pawl is preferably provided which allows movement of the ratchet member in one direction only.

Preferred aspects of the ratchet member embodiment of the invention include: arranging the teeth of the ratchet so that once the counter has reached its maximum value, no further activation is possible; providing a locking pin to prevent operation of the counter during shipping in hot climates; attaching the locking pin to the packaging of the endoscopic tool so that the locking pin is removed automatically when the tool is removed from its packaging, or alternative providing a locking pin which is automatically deactivated upon first use of the instrument; providing the counter as part of the handle of the surgical instrument or as part of a ferrule coupled to the outer tube portion of the surgical instrument; and providing the instrument with a disabling mechanism which disables use of the instrument after a predetermined number of uses.

Heat responsive mechanisms other than bimetallic strips which may be used in conjunction with a ratchet or the like are also disclosed. One such mechanism is a wax-filled cylinder and piston arrangement whereby the wax expands when melting and contracts when solidifying in order to move the piston. Another such mechanism is a gas-filled aneroid bellows which expands when heated and contracts when cooled in order to move a piston.

Other use indicators employing heat responsive means which do not use a ratchet mechanism are also disclosed. For example, one use indicator includes a source reservoir containing a colored fluid, a first one-way valve, a reservoir/pump, a second one-way valve, and a single conduit connecting to a plurality of fluid containers. As the use indicator is heated, the pump (e.g., wax plug) of the reservoir/pump expands and forces fluid contained in the reservoir through the second one-way valve into the first fluid container; thereby indicating a first use. When the use indicator cools, the wax pump contracts, and would leave a vacuum in the reservoir above the pump if not for the source reservoir. Thus, upon cooling, fluid is drawn into the reservoir/pump through the first one-way valve. Upon a second heating of the use indicator, these actions are repeated except that now that the first fluid container is full, and the fluid is forced to flow along the conduit to the next fluid container to indicate a second use.

In accord with another aspect of the invention, an electronic use indicator is disclosed. The electronic use indicator comprises one of any of a number of electronic displays such as LCD or LED devices which is coupled to an electronic counter which may be an integrated circuit and an electronic sensor such as a thermistor, diode, transistor, or the like. A preferred embodiment of the electronic use indicator includes a substantially cylindrical package containing an LCD display on its round face, a cylindrical circuit board placed behind the display and a cylindrical power cell placed behind the circuit board. The power cell is preferably a "coin cell" such as the type used in electronic watches and the entire use counter package is approximately twice the size of the power cell.

Preferred aspects of the electronic use indicator include arranging the circuit and sensor so that the display count is incremented only after the device has been heated from a preset low temperature to a preset high temperature and cooled back to the preset low temperature (i.e. one "temperature excursion"); providing a timing mechanism so that the use indicator is only incremented if a temperature excursion occurs within a preset time interval such as 15–60 minutes so that gradual temperature changes which might occur when shipping in a warm climate do not effect a use count.

Additional objects and advantages of the invention will become apparent to those skilled in the art upon reference to the detailed description taken in conjunction with the provided figures.

BRIEF DESCRIPTION OF THE DRAWINGS

FIG. 5 is a side elevation of an alternate embodiment of ratchet wheel and bimetallic pawl;

FIG. 5a is a view similar to FIG. 5 but of an alternate embodiment;

FIG. 5b is a side elevation view of the embodiment of FIG. 5a;

FIG. 6 is a side elevation view of yet another embodiment of ratchet wheel;

FIG. 7 is a side elevation schematic view of a melting-wax actuator;

DETAILED DESCRIPTION OF THE PREFERRED EMBODIMENTS

Figure 1:
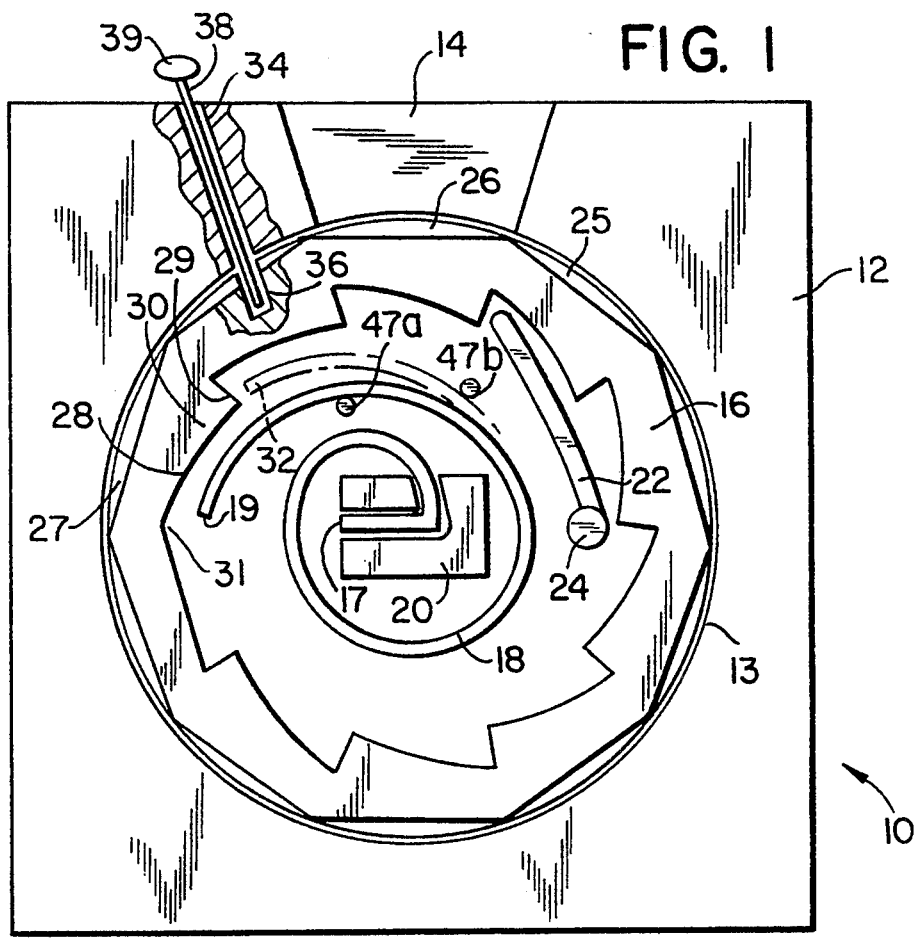
FIG. 1 is a side elevation view in partial cross section of a first embodiment of the use counter invention, where the use counter is located in a handle of a surgical instrument.
Figure 2:
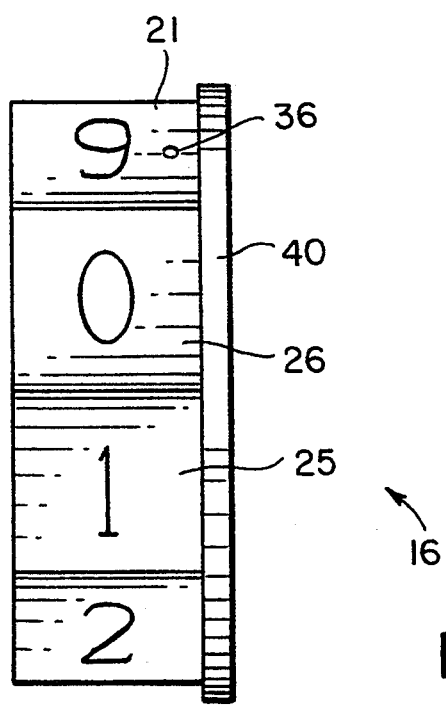
FIG. 2 is a side elevation view of the ratchet wheel of FIG. 1.

Referring now to FIGS. 1 and 2, a use counter 10 according to a first preferred embodiment invention is seen and includes a housing 12 having a generally cylindrical orifice 13, a window 14, and a rotatable ratchet wheel 16 visible through a window 14. The ratchet wheel 16 is formed as a ring with a plurality of interior teeth 30 having sloping surfaces 28, and back shoulders 29. The outer circumference of the wheel 16 is provided with a plurality of incremental indicia such as sequentially numbered facets 26. The number of interior teeth 30 is preferably one less than the number of numbered facets 26 and each facet 26 but for one 27 corresponds to an interior tooth 30. The wheel 16 is also provided with an engaging rim 40 which rotatably engages the cylindrical orifice 13 of housing 12. In order to advance the ratchet wheel 16, a bimetallic spiral 18 is provided and is anchored at one end 17 in a centrally located anchor 20 which forms part of the housing 12.

The bimetallic spiral 18 is chosen and designed so that it expands (i.e., the spiral widens) a predetermined amount when it is subjected to a predetermined temperature. For example, bimetallic spiral 18 in FIG. 1 is chosen to expand sufficiently at a temperature of 140° F. so that its free end 19 moves in a clockwise direction to the position 32 shown in phantom in FIG. 1. Of course, upon cooling, the bimetallic spiral returns to its original position shown in FIG. 1. It will thus be appreciated by those skilled in the art that when the counter 10 is subjected to sterilization temperatures, the bimetallic spiral 18 will expand, and possibly ride over a sloping surface 28, and then snap behind a shoulder 29 of a tooth 30 of the wheel 16. If the spiral 18 contacts the sloping surface 28 as it expands, wheel 16 will not be moved in the clockwise direction, because a second pawl 22 is provided to prevent such clockwise rotation. As seen in FIG. 1, pawl 22 is mounted by a pin 24 to the housing 12 between the spiral 18 and the toothed interior of wheel 16 so that it is biased towards and will engage the shoulder 29 of a tooth 30 of the ratchet. Thus, as ratchet wheel 16 rotates counterclockwise, pawl 22 rides along the sloped surface 28 and falls behind shoulder 29. However, if the wheel 16 starts rotating clockwise, pawl 22 jams into the shoulder 29 and prevents it from doing so.

As aforementioned, when the bimetallic spiral is heated, it expands and causes its free end 19 to fall behind a tooth shoulder 29. However, when sterilization is complete and the counter (and bimetallic spiral) cools, the spiral 18 will attempt to return to its original position. Because the free end 19 of the bimetallic spiral is located behind the tooth shoulder 29, upon cooling, the bimetallic spiral acts on the tooth shoulder and thereby rotates wheel 16 in a counter clockwise direction. By carefully dimensioning the spiral 18 and by providing each facet with a corresponding tooth 30, the wheel 16 will be rotated one facet each time the counter is sterilized. If desired, in order to reduce criticality in dimensioning, limiters or stops 47a and 47b can be provided. Limiter 47a which is located between the hub 20 and the outer portion of bimetallic strip 18 limits the coiling motion of the bimetallic spiral as it cools, thereby preventing the bimetallic strip from pushing the ratchet wheel 16 too far forward. Limiter 47b, on the other hand, is located between the bimetallic strip 18 and the ratchet wheel 16, and limits the opening of the bimetallic spiral as it heats, thereby preventing the free end 19 of the bimetallic strip from moving too far backward (e.g., behind two or more teeth).

Because the use counter is intended for medical instruments which should be used only a limited number of times, it is desirable that the counter should stop advancing after it has been sterilized that number of times (i.e., the medical instrument should be discarded). Thus, the counter should ideally advance from a starting position, for example where the numeral zero (zero previous uses) of a facet 26 is shown through window 14, to a position where the numeral one of a facet 25 is seen through window 14, and so on until a facet (e.g., facet 21) which indicates that the instrument has been used the maximum desired number of times is exposed through window 14. At that point, the ratchet wheel should advance no further. In order to prevent the ratchet wheel from further advancement (i.e., to the position showing numeral zero again), a shallow surface 31 is provided adjacent facet 27 in place of a tooth 30 to prevent the wheel 16 from being rotated beyond the position where facet 21 is exposed through window 14. Thus, when the last facet indicating the highest number of sterilizations is exposed through window 14, the shallow surface 31 assumes a position relative to the free end 19 of bimetallic spiral 18 such that there is no tooth shoulder which free end 19 can engage when spiral 18 expands.

Since temperatures as low as 140° F. may be used in ETO sterilization, care must be taken not to expose the counter to these temperatures other than during sterilization lest an erroneous count be registered. This is particularly problematic during transportation of the medical instruments in climates where the ambient storage temperature of the instruments may reach 140° F. or higher. In order to prevent activation of the counter during storage and transport prior to its initial use, a locking pin 38 is provided. The locking pin 38 is shown extending through and received by a bore 34 in the housing, and ratchet wheel 16 is preferably further provided with a locking bore 36, for example as shown in facet 21 which receives the pin 38. When in place, pin 38 prevents advancement of the wheel 16.

Figure 4:
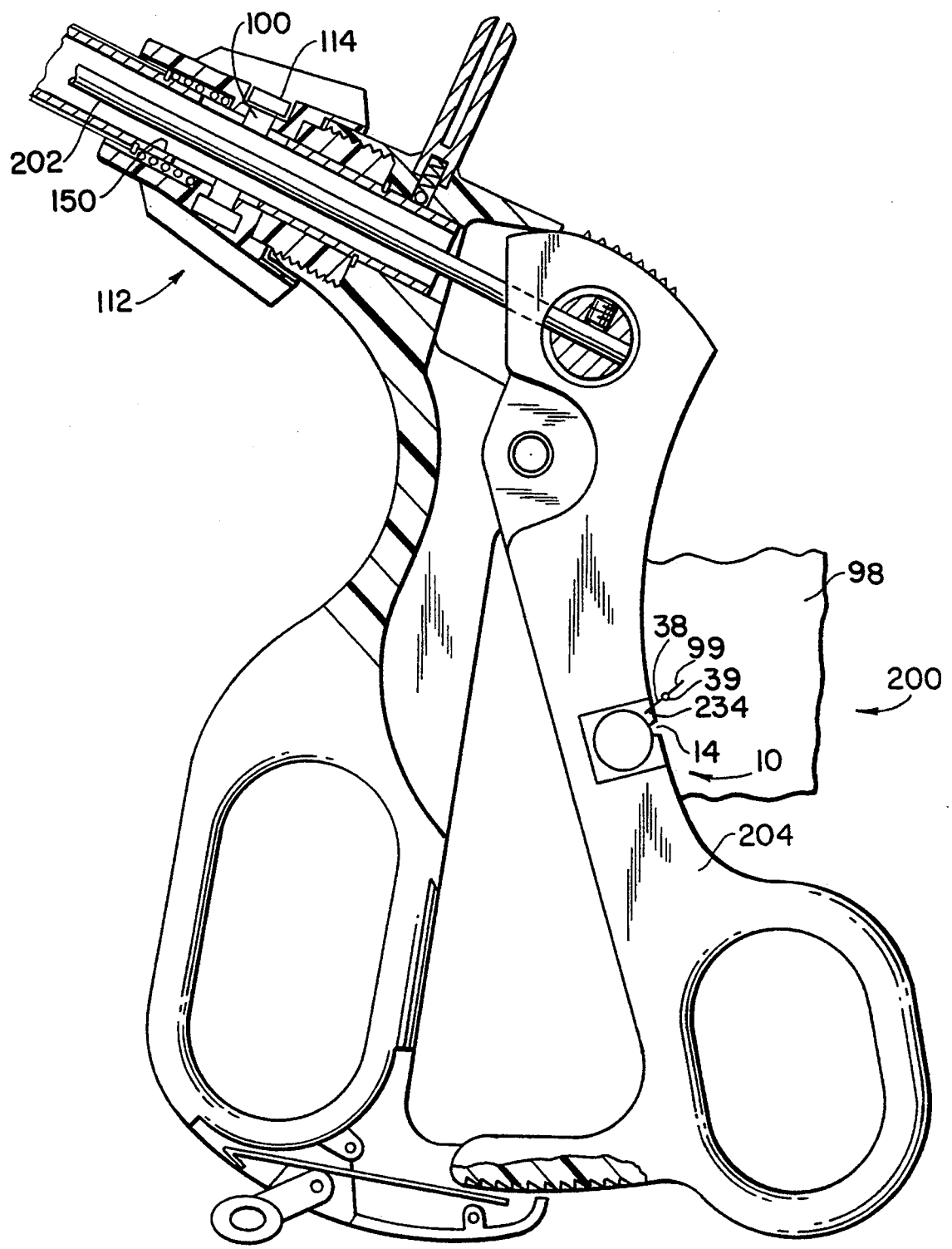
FIG. 4 is a perspective view of an endoscopic instrument showing preferred locations for the first two embodiments of the invention.

It will be appreciated that prior to use of the medical instrument, the pin 38 should be removed and discarded. FIG. 4 shows the proximal portion of an endoscopic tool 200 with the counter 10 built into the handle portion 204. There it can be seen that the locking pin 38 extends through a bore 234 in the handle and is provided with a pull ring 39 extending out of the handle which can be attached to the packaging 98 of the tool with a staple 99 or the like. This arrangement guarantees that the locking pin 38 is automatically removed when the tool 200 is removed from its package.

Figure 3:
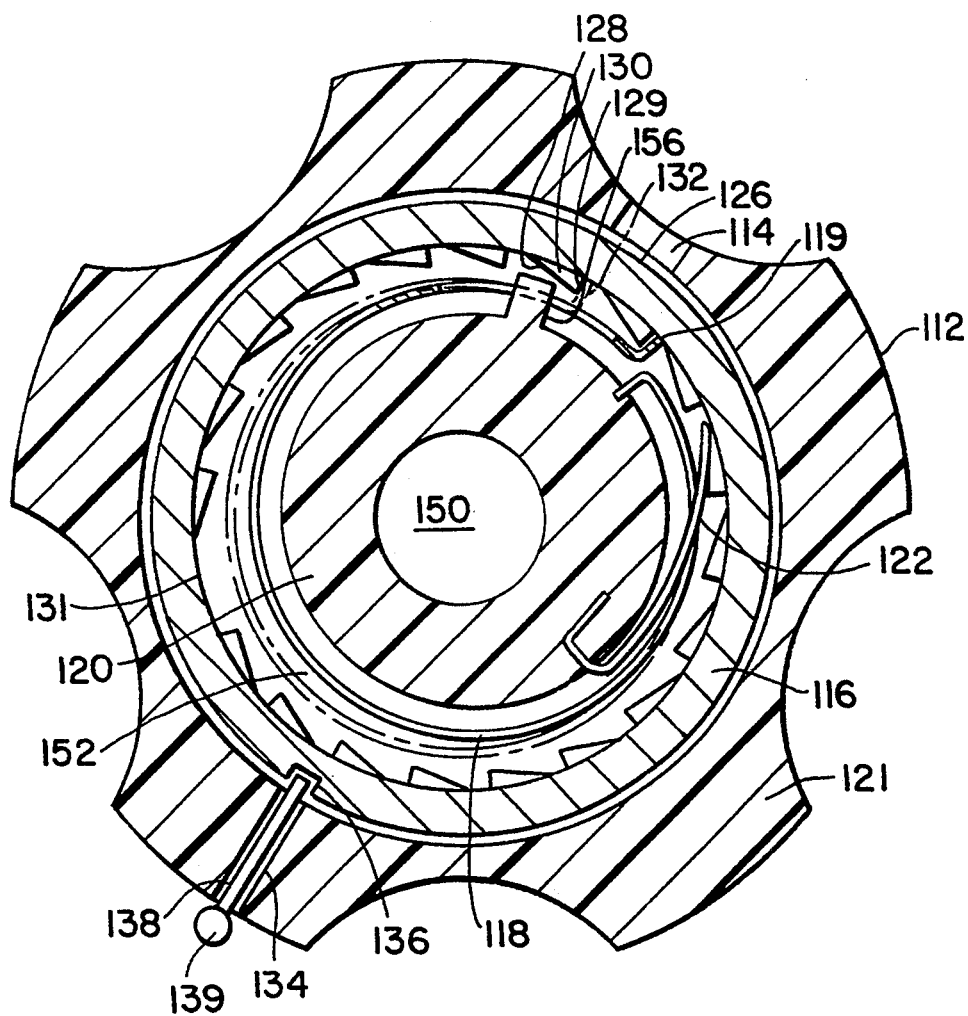
FIG. 3 is a cross sectional view of a second embodiment of the use counter invention, where the use counter is located in the ferrule of a surgical instrument.
Figure 3A:
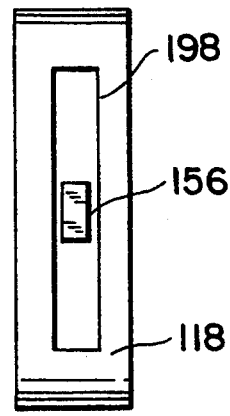
FIG. 3a is a close detail of the bimetallic ring and guide boss.

Turning now to FIG. 3, a second embodiment of the invention is shown. Here the counter 100 of the invention is built within a ferrule 112 (see also FIG. 4) which is described in detail in co-assigned U.S. Pat. No. 5,174,300 the complete disclosure of which is incorporated herein by reference. Here, ferrule 112 is further provided with a window 114 and a radial locking pin bore 134 which serve the same functions as the window 14 and bore 34 in the embodiment of FIG. 1. A ratchet wheel 116 in the form of a ring is mounted coaxially within the ferrule 112 and rotatable with respect to it. The ratchet wheel 116 is provided with a plurality of interior teeth 130 with sloping surfaces 128 and shoulders 129, and the outer surface of the wheel 116 is provided with incremental indicia 126. The number of teeth 130 is preferably chosen to be one less than the number of indicia 126 for the same reason as stated above with reference to FIG. 1. A bimetallic ring 118 which acts as a pawl for the ratchet wheel 116 is mounted at one end 117 in a hub 120 of the ferrule 112. Hub 120 is preferably eccentrically located relative to the outer portion 121 of the ferrule 112. The hub 120 surrounds and is preferably attached to tube 150 of the endoscopic instrument which surrounds the push rod (202 in FIG. 4) which in turn is coupled to the end effectors (not shown) of the endoscopic instrument. As shown in FIG. 3, the bimetallic ring 118 surrounds almost 360° of the hub 120 so that its bent end 119 engages the shoulder 129 of a tooth 130 in the vicinity of its mounted end 117. In order to hold, guide, and limit the movement of the bimetallic ring 118, a movement limiting guide boss 156 is provided on the hub 120 near the bent end 119 of the bimetallic ring 118. A detailed view of guide boss 156 is shown in FIG. 3a where it can be seen that the bimetallic ring 118 is provided with a slot 198 into which boss 156 extends. Expansion and contraction of the ring 118 is thereby limited by the boss 156 as it engages the edges of slot 198. A second pawl 122 is also mounted in the hub 120 and functions substantially the same way as pawl 22 described above with reference to FIG. 1.

Bimetallic ring 118 preferably is chosen to expand a predetermined amount at a predetermined temperature as was described above with reference to the bimetallic spiral 18 of FIG. 1. In this second embodiment, however, as ring 118 expands, its bent end 119 moves forward (counterclockwise) in the limiting guide boss 156 as shown in phantom. In this manner, as the bimetallic ring heats up, it advances the wheel 116 counterclockwise with the end of the ring as shown at 132 pushing the tooth 130 forward. When the ring cools and compresses, the bent end 119 of the bimetallic ring 118 rides up over the ramped surface 128 of the tooth 130 until it falls behind the shoulder 129 and returns to its original position now behind a clockwise adjacent tooth 130. As the bent end 119 of ring 118 rides up over the ramped surface 128 of the tooth 130, the wheel is prevented from rotating clockwise because of the action of pawl 122.

The hub 120 of ferrule 112 is preferably located in an eccentric manner relative to tube 150 so that a larger space 152 lies between it and the interior of wheel 116 at a point approximately 180° from the point where mounted end 117 of ring 118 is secured in hub 120. This space provides room for the expansion of ring 118.

As with the embodiment of FIG. 1, a shallow surface 131 is provided at a preselected position in place of a tooth 130. The shallow surface 131 prevents the wheel 116 from being rotated beyond the position where the last use indicia is exposed through window 114.

For the same reasons as mentioned above regarding the embodiment of FIG. 1, counter 100 is also preferably provided with a locking pin 138 which is received by bore 134 in ferrule 112 and in bore 136 in wheel 116. The locking pin 138 prevents movement of the wheel during shipping. As in the embodiment of FIG. 1, the locking pin is ideally provided with a pull ring 139 which can be attached to the packaging of the tool.

FIG. 4 shows a partial view of the proximal portion of an endoscopic tool 200 with both embodiments of the invention appearing schematically. In this example, the embodiment 10 of FIG. 1 is mounted within the handle portion 204 of the tool although it could be mounted elsewhere. The embodiment 100 of FIG. 3 is mounted in the ferrule 112 as described above. While FIG. 4 shows both embodiments of the invention installed in the same tool for illustration purposes, only one of the counting mechanisms need be installed on the tool. However, if the medical instrument has handles or portions which may be uncoupled from other portions of the instrument, such as might be possible with endoscopic surgical instruments, it might be desirable to provide one or both (or more) portions with their individual use counters. Indeed, where an endoscopic surgical instrument has separate mating handle and distal portions, a pre-use locking mechanism could be provided for the use counter, where before the mating of the handle and distal portions, the locking mechanism prevents erroneous triggering of the counter, and upon mating of the handle and distal portions, the counter is automatically activated.

Turning now to FIG. 5, an alternate embodiment of a ratchet wheel and bimetallic pawl is shown. Here the ratchet wheel 520 is centrally located with exterior teeth 530, and the bimetallic pawl 518 engages the teeth 530 of the ratchet from the outside. As shown in FIG. 5, the bimetallic pawl 518 is coupled to the rotating display member 516 while the ratchet wheel 520 remains stationary. A direction limiting pawl 522 engages the rotating member 516 so that it can be advanced in one direction only as indicated by the arrow; in this case counterclockwise. As the bimetallic pawl 518 expands when heated, its free end 519 presses against shoulder 529 of a tooth 530 thereby advancing the rotating display member 516 in a counterclockwise direction. The dimensions of the pawl 518 are chosen so that its expansion advances the display member 516 a predetermined amount. When the bimetallic pawl 518 cools, it contracts, and its free end 519 slides up over the sloping surface 528 of a next tooth 530 to rest against a next shoulder 529. In this manner, the bimetallic pawl 518 is ready to advance the display member again when heated. The similarities and differences between this embodiment and the embodiments described above with reference to FIGS. 1–3 will now be apparent to those skilled in the art. For simplicity, some of the similar features of this embodiment have not been shown in the drawing, but it will be appreciated that a window, locking pin, missing tooth, etc. can and would be applied to this embodiment as well.

FIGS. 5a and 5b show an embodiment similar to the embodiment of FIG. 5, but here the centrally located ratchet wheel 520 is not stationary and is laterally coupled to a display wheel 516 as seen in FIG. 5b, and the bimetallic pawl 518 is coupled to a fixed outer housing 512. Direction limiting pawl 522 engages the teeth of the ratchet wheel 520 so that incremental movement of the display means 516 is in the clockwise direction as shown. When the bimetallic pawl 518 is heated, its free end rides over a tooth; while when the bimetallic pawl 518 cools, its free end pushes the tooth, and hence the wheel 520 forward (clockwise). When the wheel 520 rotates clockwise, the display wheel 516 likewise rotates to display a new number. Having the benefit of the above disclosure, it will be apparent to those skilled in the art how this embodiment differs from the embodiments disclosed above. For simplicity, some of the similar features of this embodiment have not been shown in the drawing, but it will be appreciated that a window, locking pin, missing tooth, etc. can and would be applied to this embodiment as well.

Figure 8:
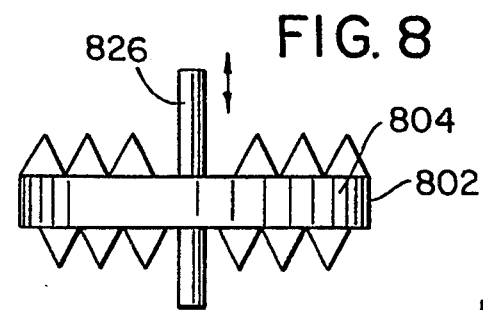
FIG. 8 is a side elevation schematic view of a sealed gas aneroid bellows actuator.

FIG. 6 shows yet another type of ratchet wheel for incremental rotation of a display surface. In this embodiment, the ratchet wheel 616 operates according to principles similar to an escapement wheel in a clock. The wheel 616 is provided with exterior teeth 630 and preferably is biased in a counterclockwise direction by a main spring 621 coupled to a hub 620. Rotation of the wheel is prevented by a first pawl 624 which rests against the shoulder 629 of a tooth 630 and which is biased by a pawl biasing spring 622. First pawl 624 is pivotally coupled with a spaced apart second pawl 625. An impulse or reciprocating connection 626 allows an impulse or reciprocating member such as a piston (examples of which are described below with reference to FIGS. 7 and 8) to move second pawl 625 towards the wheel 616. When second pawl 625 is moved towards the wheel 616, its coupling with the first pawl 624 about the pivot 623 causes the first pawl 624 to move away from wheel 616, thereby compressing spring 622. Pawls 624 and 625 are dimensioned and placed relative to wheel 616 such that as pawl 624 is moved away from the wheel, the wheel under action of main spring 621 is permitted to advance one half an increment (e.g., typically one-half or one full tooth) until it is stopped by the second pawl 625 which engages the shoulder 629 of another tooth 630. When the force applied to connection 626 is released, the spring 622 acts to move the first pawl 624 towards the wheel, thereby pivotally moving second pawl 625 away from the wheel. The wheel is thus permitted to advance another half increment in the interval between pawl 625 disengaging a tooth and pawl 624 engaging a tooth. With the benefit of the disclosure herein, those skilled in the art will appreciate how this embodiment of an incremental advancement device can be applied to the display described above. In order to incorporate this device in a sterilization counter, it is only necessary to supply a heat responsive device which will apply the impulsive force to connection 626. FIGS. 7 and 8 which are discussed in detail hereinafter, show two embodiments of heat responsive devices which can supply an impulse or reciprocating force to the connection 626. One notable feature of this embodiment is that the display is incremented only after a full cycle of heating and cooling.

It should also be noted that if the heat responsive device coupled to 626 is a bidirectional or reciprocating device (pushes and pulls rather than only impulse pushing), the springs 621 and 622 may be omitted. With a bidirectional heat responsive device, when the device is heated and force is supplied to connection 626, thereby pushing second pawl 625 towards sloping surface 628 of a tooth 630. As the second pawl 625 engages the sloping surface of the tooth 630, it rides along the surface and advances the wheel 616 one half an increment. As the second pawl 625 engages the sloping surface 628, the first pawl 624 disengages shoulder 629 of the next counter-clockwise adjacent tooth, thereby freeing the wheel 616 to be advanced by the second pawl 625. When the bidirectional heat responsive device is cooled, a pulling force is applied to connection 626 and, through pivot 623, the first pawl 624 is pushed towards wheel 616 to engage a sloping surface 628 and advance the wheel 616 another half an increment. The alternating action of pawls 624 and 625 advance the wheel and prevent it from turning backwards.

It should be appreciated that the escapement mechanism described with reference to FIG. 6 is not limited to the advancement of the wheel by one half an increment. Thus, during the heating, the advancement can be from a small part of an increment to an almost complete increment, with the remainder being provided during cooling. Also, an "increment" should not be interpreted as a single tooth, as depending upon the placement of the indicia, an "increment" may comprise one, two, or a different number of teeth.

FIG. 7 shows a heat responsive force supplier which might be used with the escapement mechanism of FIG. 6. The force supplier of FIG. 7 includes a container 702 filled with wax 704 which opens to a cylinder 706 containing a piston 708 therein. A piston rod 726 is coupled to piston 708 at one end and may be coupled to the connection 626 of FIG. 6 at its other end. When heated, the wax 704 melts and expands into the cylinder 706, thereby forcing piston 708 and thus piston rod 726 outward. When the wax cools, it contracts and flows back from the cylinder 706 into the container 702, thereby allowing piston 708 and piston rod 726 to return to their initial position. As aforementioned, it will be appreciated by those skilled in the art how this heat responsive device can be used to actuate the escapement device of FIG. 6.

Figure 8A:
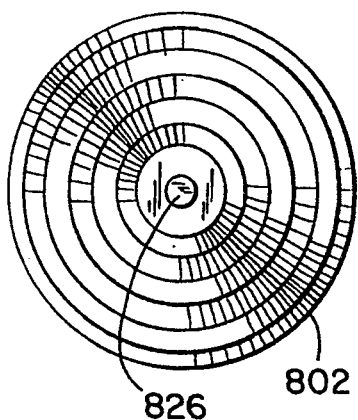
FIG. 8a is a top plan view of the actuator of FIG. 8.

FIGS. 8 and 8a show a sealed aneroid bellows 802 containing a gas 804 and coupled to a plunger 826. When heated, the gas 804 in the bellows 802 expands to move the plunger 826 outward, and when the gas cools, the gas contracts in the bellows 802 moving the plunger 826 inward. It will be appreciated by those skilled in the art how this heat responsive device can be used to actuate the escapement device of FIG. 6.

Figure 9:
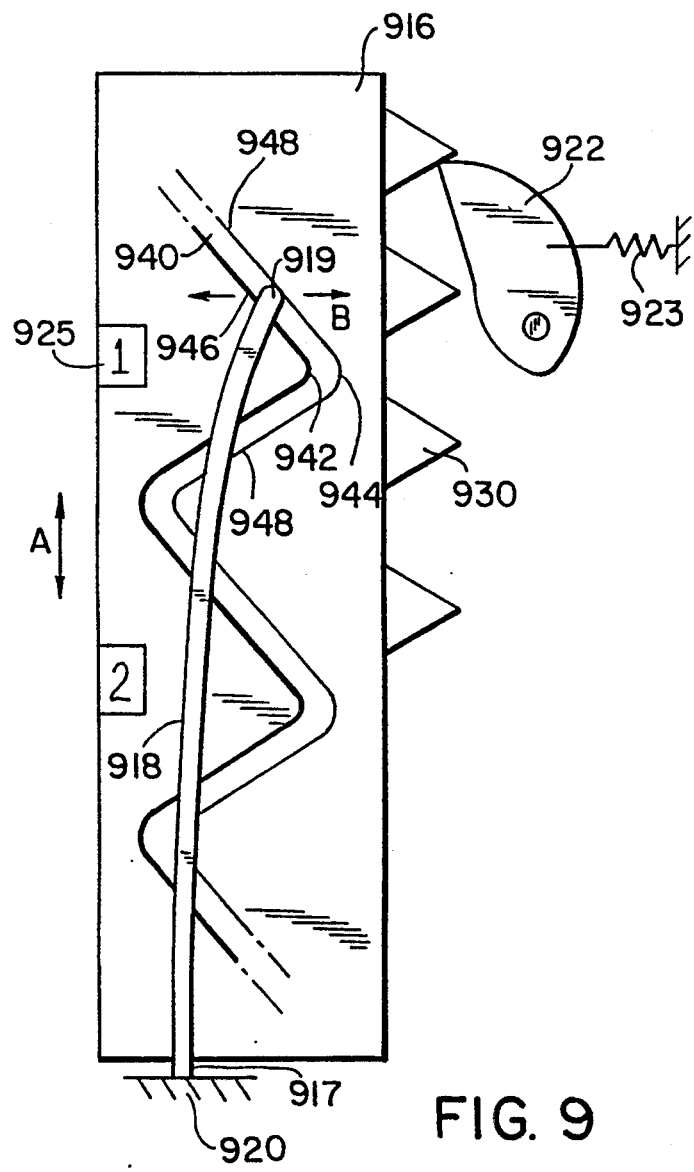
FIG. 9 is a side elevation schematic view of a slotted strip ratchet member driven by a bimetallic element.

FIG. 9 shows a different embodiment of a ratchet member advanced by a bimetallic member. Here, the ratchet member is not a wheel, but a strip 916 which moves up or down as shown by arrows A in FIG. 9. The strip 916 is provided with a "zigzag" slot 940 which is engaged by the free end 919 of a bimetallic member 918. Bimetallic member 918 is fixed to stationary coupling 920 at its other end 917 and is designed to bend toward the right as shown by the arrow B in FIG. 9 when it is heated, and return upright when cooled. A direction limiting pawl 922 biased by a spring 923 engages teeth 930 on a side of the strip 916 so that the strip may be advanced in only one direction; in this case up. Indicia 925 are provided on the strip for the same purpose as described above with reference to FIGS. 1–3. The slot 940 is dimensioned with walls 946, 948 and bends 942, 944 so that sideways movement of the bimetallic member 918 advances the strip through the engaging action of free end 919 biasing walls 946, 948. For example, when heated, the bimetallic member 918 bends to the right, with its free end 919 engaging wall 948, and causes strip 916 to move up against the pawl 922 which prevents downward movement of the strip while allowing upward movement. The bimetallic member 918 continues its rightward bend until it engages turn 944 in the slot 940 whereupon it can move no further. Upon cooling, the bimetallic member 918 starts straightening so that its free end 919 engages wall 946 of slot 940. By placing bend 942 higher than bend 944, the engagement of wall 946 by free end 919 of bimetallic member 918 causes the strip 916 to advance further. The movement of strip 916 further upwards continues until the bimetallic member 918 straightens completely and locates itself in the next bend. It is of note, that as with the escapement embodiment described above, this embodiment has the feature that the display is incremented only after a full cycle of heating and cooling. It is also of note, that because the strip 916 advances in a forward direction (rather than circularly), this embodiment could be particularly useful in impeding the use of an endoscopic surgical instrument after its last intended use, such as by causing the strip to advance into a position which impedes handle movement or which impedes the motion of a push rod. Of course, arrangements utilizing the rotating counter could also be provided to automatically impede usage of the medical instrument after the last intended use.

All of the embodiments described so far involve a substantially mechanical device. Although not shown in detail, it will be appreciated that a mechanical disabling device could be coupled to the counter so that the surgical instrument is disabled or its function impaired after it has been sterilized a certain number of times.

Figure 10:
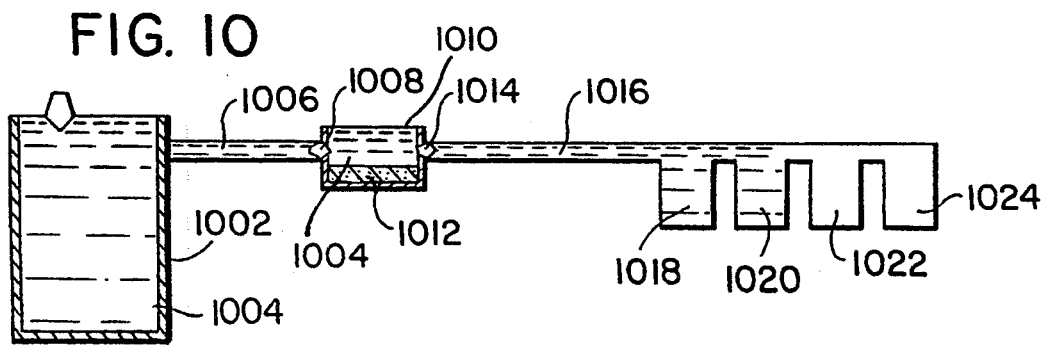
FIG. 10 is a side elevation schematic view of a fluid vessel indicator.
Figure 11:
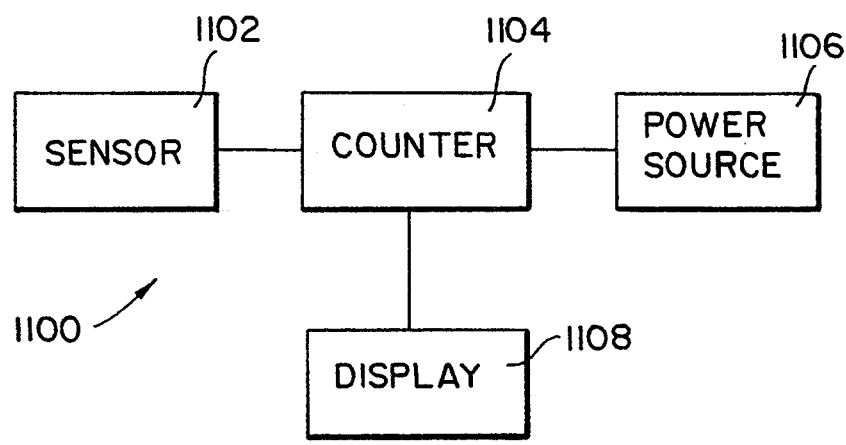
FIG. 11 is a schematic block diagram of an electronic use counter.

FIG. 10 shows an apparatus for counting heating cycles which utilizes fluid mechanics and does not increment via a mechanical mechanism. The embodiment of FIG. 10 includes a fluid container 1002 containing a fluid 1004.

Container 1002 is coupled to a measuring reservoir/pump 1010 by a conduit 1006 and a one-way valve 1008 which allows fluid 1004 from container 1002 to enter the reservoir 1010 through conduit 1006 but prevents fluid 1012 from exiting reservoir/pump 1010 through conduit 1006. The reservoir/pump is preferably a container which includes a self-contained expanding bottom pump portion containing wax 1012 or the like. In this manner, the bottom pump portion expands when heated. The reservoir/pump 1010 is further coupled to a conduit 1016 through a second one-way valve 1014 which allows fluid 1012 to flow from the reservoir 1010 into the conduit 1016. The conduit 1016 is coupled to a series of indicator fluid containers 1018, 1020, 1022, 1024, which are located sequentially downstream along the conduit 1016.

In use, when the medical instrument with the heat cycle counter of FIG. 10 is heated, the wax in the pump portion of reservoir/pump 1010 expands and forces whatever fluid was located in the reservoir portion of the reservoir/pump 1010 past one-way valve 1014 and into the fluid conduit. By providing enough fluid in the reservoir of reservoir/pump 1010, one of the indicator fluid containers 1018 will at least partially fill and indicate a first use of the medical instrument. When the medical instrument cools, one-way valve 1014 prevents the fluid from returning into the reservoir of the reservoir/pump 1010. However, so that a vacuum is not formed in the reservoir of the reservoir/pump, fluid 1004 from the container 1002 will be provided through conduit 1006 and valve 1008. If desired, in order to guarantee flow from the container 1002 into the reservoir/pump, the container 1002 may be provided with a piston or relief (not shown) which is subject to the ambient. It will be appreciated that the dimensions of the containers, reservoir, and conduits, as well as the volume of fluid in the apparatus are chosen so that fluid exiting reservoir/pump 1010 is sufficient to fill only one indicator container. Therefore, each time the medical instrument is heated to the appropriate temperature, the pump 1010 pumps enough fluid so that the next downstream indicator container 1020, 1022, 1024, etc is filled. It will also be appreciated that depending on the dimensions of the conduits and the volume of fluid, the indicator containers 1020, 1022, 1024 may be omitted and the conduit may simply be marked with use indicia similar to thermometer tube markings.

FIGS. 11, 12a, 12b and 12c show an electronic embodiment of the invention; i.e., an electronic temperature cycle counter 1100. The electronic temperature cycle counter 1100 shown schematically in FIG. 11 generally includes a sensor 1102 such as a thermistor, diode, transistor, integrated circuit (IC) or the like which is sensitive to changes in temperature, and which changes its electrical properties in response to changes in temperature. The sensor is coupled to an electronic counting circuit 1104 which in turn is coupled to a power source 1106 and a display 1108 such as an LCD. The counting circuit 1104 may be an integrated circuit combining a counter and an LCD driver or a microprocessor. The power source 1106 is ideally a "coin cell" (carbon-zinc, silver-oxide, lithium-iodide, etc.). The LCD display 1108 may be either a seven segment numeric display or a special symbol display. The counter circuit 1104 is designed to register a change in the display after the sensor senses a "temperature excursion", i.e., a change in temperature from a preset low temperature to a preset high temperature and back to the low temperature. If an oscillator is used in conjunction with the counter circuit, the counter circuit 1104 can be arranged to register a change in the display only if the temperature excursion occurs within a preset time interval (for example the typical 15 to 60 minutes of autoclaving or other sterilization) in order to prevent an erroneous registration of temperature excursion due to a gradual temperature change during shipment in warm climates.

Figure 12A:
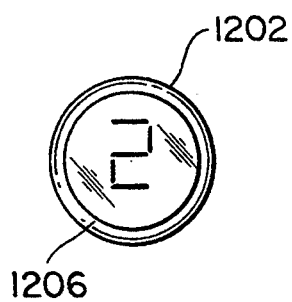
FIG. 12a is a front view of a packaged electronic use counter.
Figure 12B:
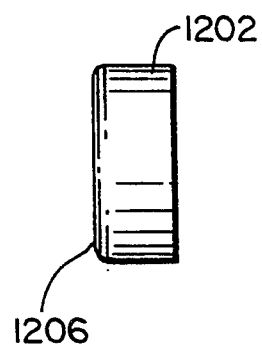
FIG. 12b is a side view of a packaged electronic use counter.
Figure 12C:
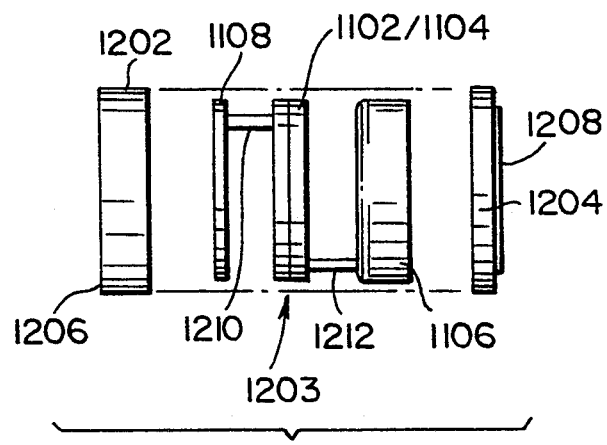
FIG. 12c is an exploded side elevation view of a packaged electronic use counter.
Figure 13:
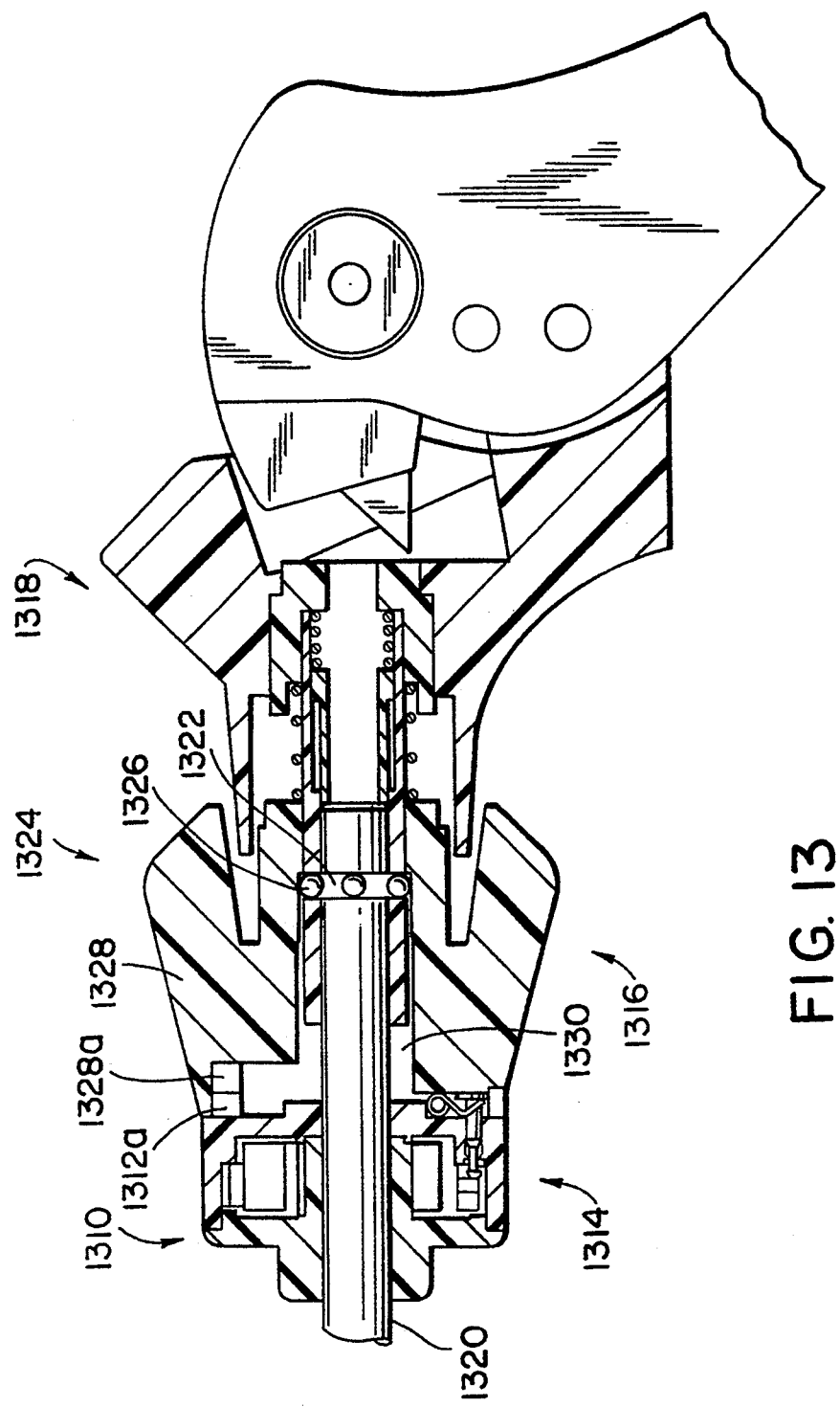
Figure 14:
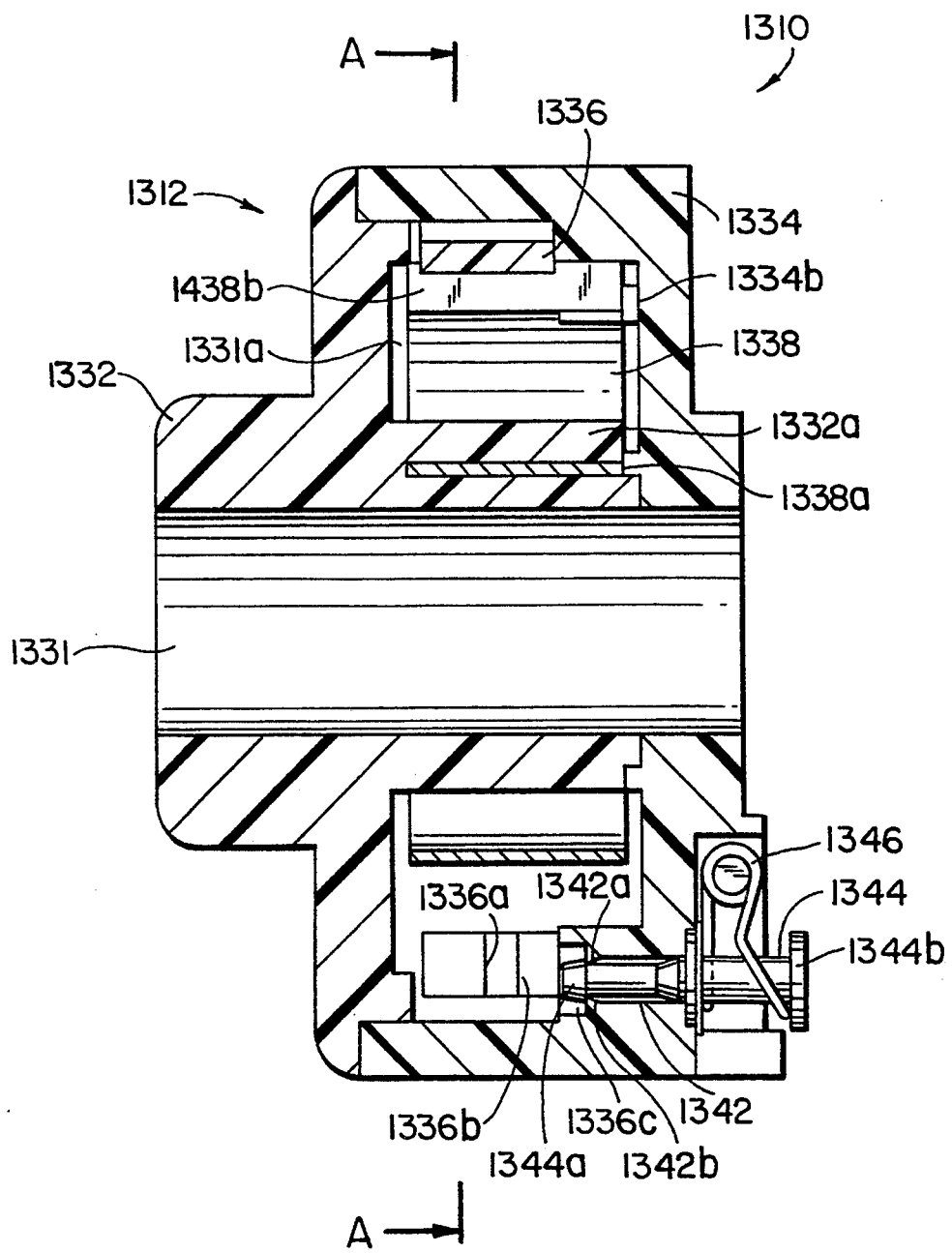
Figure 14A:
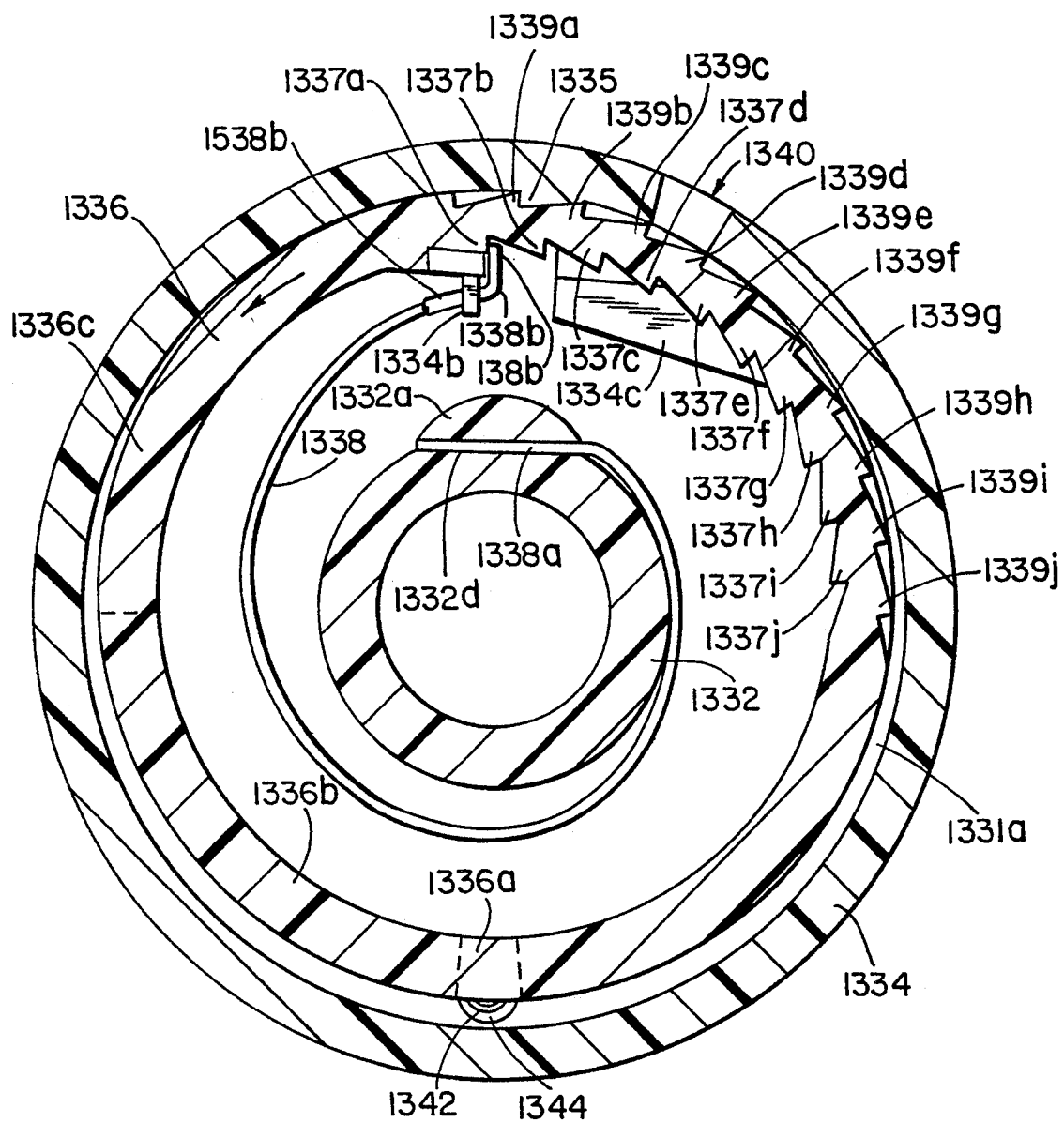
Figure 14B:
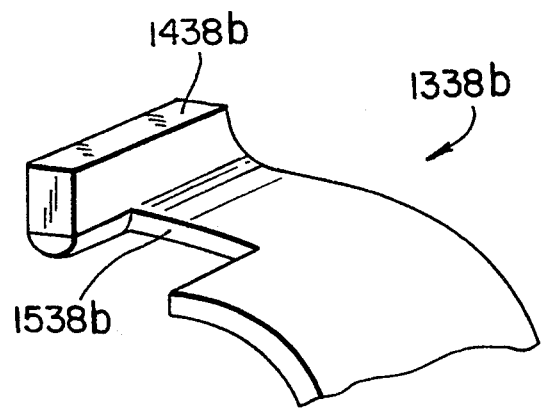
Figure 14C:
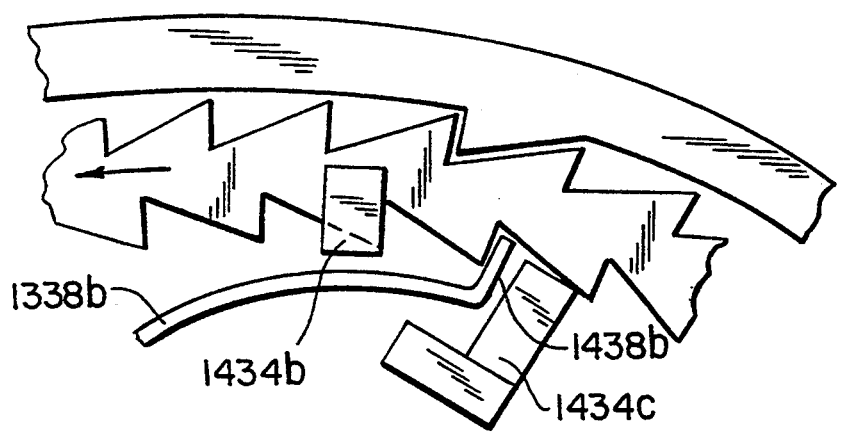
Figure 15A:
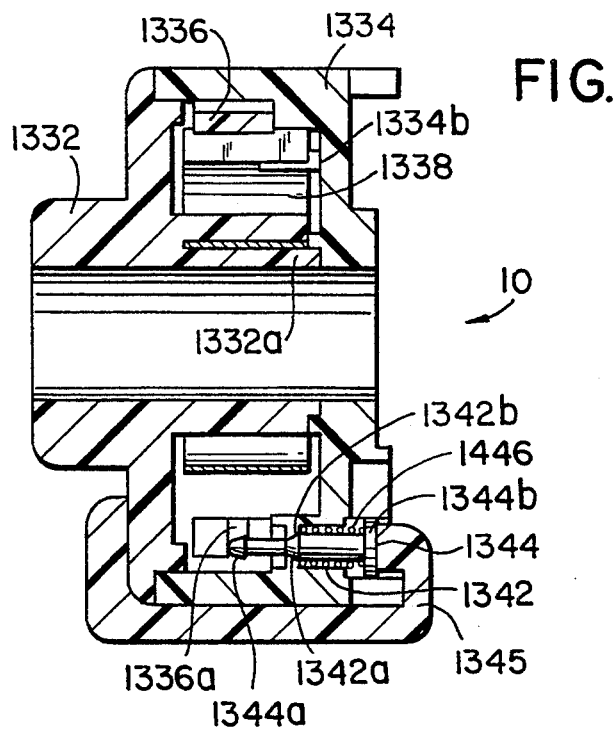
Figure 15B:
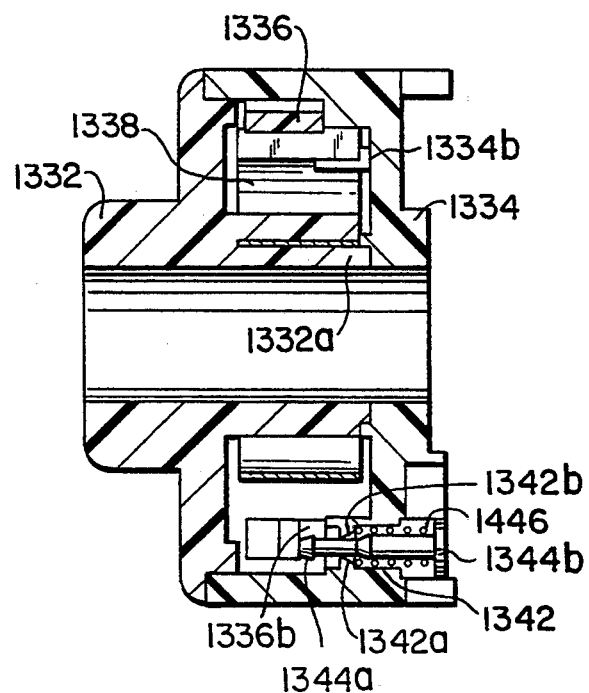
Figure 15C:
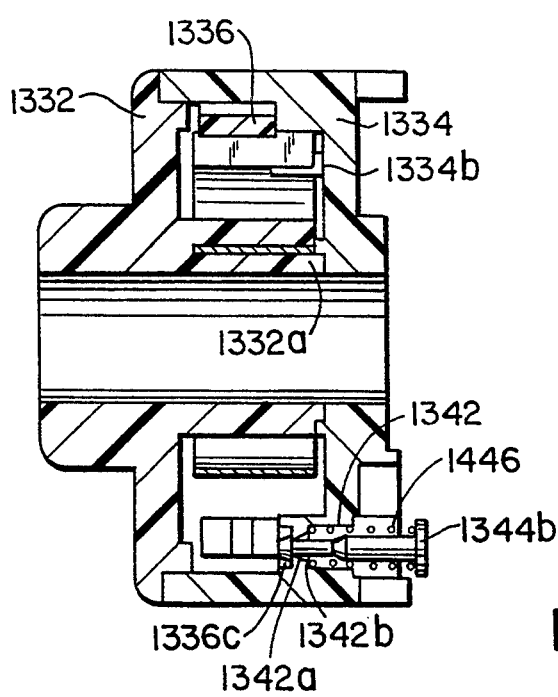
Figure 16A:
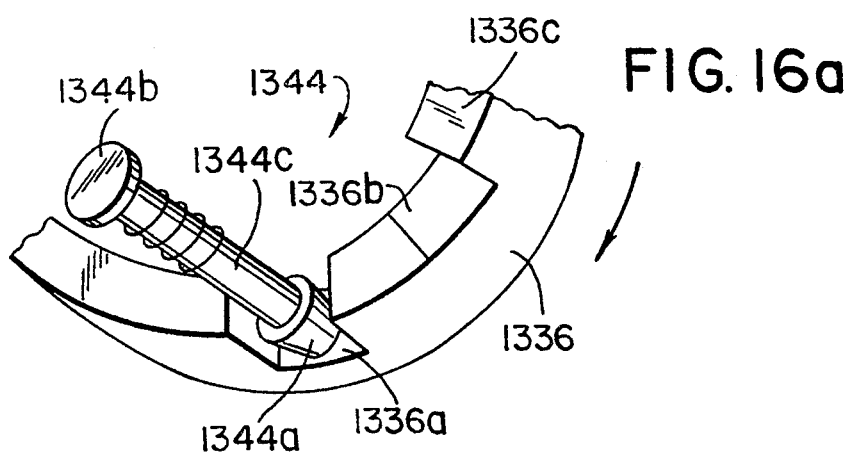
Figure 16B:
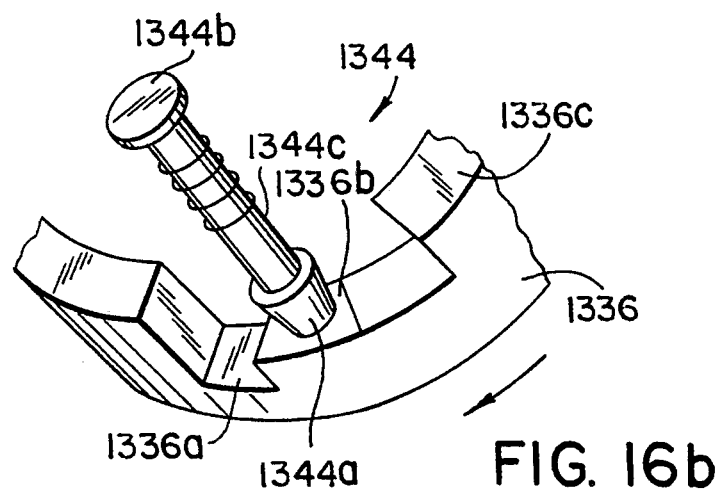
Figure 16C:
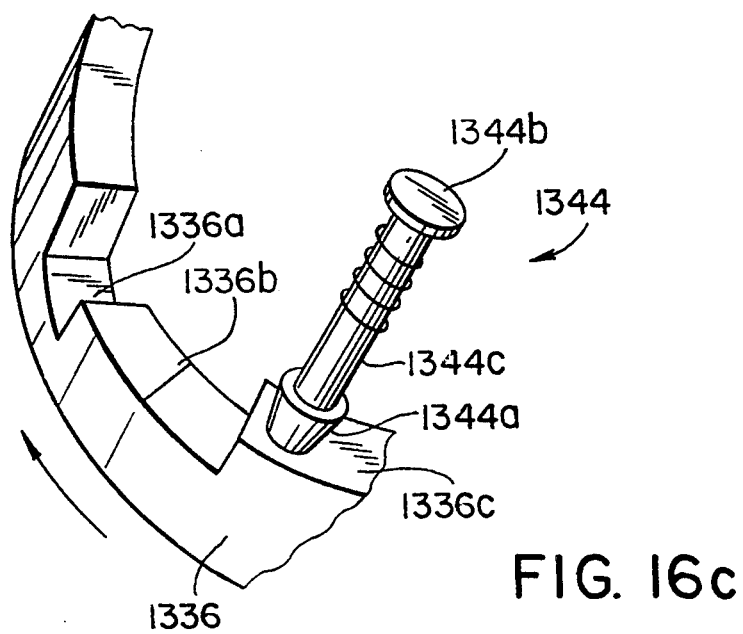

FIGS. 12a–12c show a preferred packaging of the electronic temperature cycle counter 1100. A generally cylindrical container 1202 contains a sandwich of the LCD 1108, a miniature circuit board 1203 containing both the sensor 1102 and the counter circuit 1104, and the power cell 1106. The container is open faced with a retaining rim 1206 against which a self-contained LCD display disk 1108 is secured within the container. The circuit board 1203 containing both the sensor and the counter circuit is dimensioned to approximately the same diameter as the display disk and packed behind the display in the cylindrical container 1202. The display is coupled to the circuit board by wire connectors 1210, but may be connected in other ways such as biased contacts which couple when the pieces are pressed together, or directly by soldering. A disk shaped power cell 1106 is likewise packed behind the circuit board, and the power cell is also coupled to the circuit board by wire connectors 1212 as shown or in other ways known to those skilled in the art. The entire sandwich of the LCD, circuit board 1203, and power cell 1106 is enclosed within the cylindrical container 1202 by a rear cover 1204 which screws in place. The outside of the rear cover is preferably provided with a peel-and-stick self-adhesive strip 1208 so that the counter may be affixed to a medical instrument so that sterilizations of the medical instrument may be counted. Alternatively, if a cylindrical bore is provided in the medical instrument (e.g., in the handle), the electronic counter 1100 may be placed in the bore, with or without a window over the counter.

There have been described and illustrated herein several embodiments of a use counter which counts the number of times a medical instrument has been used (sterilized). While particular embodiments of the invention have been described, it is not intended that the invention be limited thereto, as it is intended that the invention be as broad in scope as the art will allow and that the specification be read likewise. Thus, while particular incremental indicia in the form of numbers have been disclosed, it will be appreciated that other indicia could be utilized. For example, a color code could be used (e.g., a sequence of colors, or no color and then red, or all black then red, etc.), dots could be used, or the indicia could be in reverse order to indicate the number of reuses available rather than the number elapsed. In addition, instead of a number, the words "last use" might appear in the window for the last intended use (so as to avoid an unnecessary sterilization process), and a warning (e.g., "please discard", or a red marker, etc.) might appear in the window if the medical instrument is sterilized after its intended last use. Also, while certain configurations of a ratchet wheel have been shown, it will be recognized that other configurations could be used with similar results obtained. For example, the outer surface of the wheel could be either faceted or smoothly cylindrical or a combination of those. Moreover, while particular configurations have been disclosed in reference to teeth, it will be appreciated that other configurations could be used as well.

As to the bimetallic heat responsive member, it will be appreciated that advancement of the indicia may be effected either upon heating or cooling or only upon a complete temperature excursion. Therefore, with the benefit of the instant disclosure, it will be understood how various features of the different embodiments could be combined to create yet additional embodiments. The bimetallic member may be used with the escapement ratchet or the impulse supplying devices described with reference to the escapement device may be applied to the other ratchet devices.

It will further be appreciated by those skilled in the art that in the escapement embodiment, it may be possible to provide different actuation means other than those shown and described. In addition, it will be appreciated that the terms "clockwise" and "counter clockwise" have relative meaning only and the ratchet wheel could be arranged to rotate in either direction. Furthermore, while the locking bore and locking pin have been disclosed as having a particular location and configuration, it will be understood that different types of locking means can achieve the same or similar function as disclosed herein. Similarly, while the counting mechanisms have been described as being located in certain locations such as the handle, or the ferrule, it will be appreciated that the counting mechanism could be located anywhere on the medical instrument, provided it is attached to the medical instrument or incorporated therein in such a manner so that it will be subjected to heat changes when the medical instrument is sterilized.

In the fluid mechanical embodiment, it will be appreciated that the number of containers and the volume of fluid will depend on the number of uses to be counted. In the electronic embodiment, it will be appreciated that the exact circuitry and packaging of the counter may be varied according to need and/or economics. In particular, the counter circuit and the display driver circuit may be integrated or kept separate depending the economics of manufacture. The display may be a segmented numeric LCD display or any other suitable display having sequential indicia.

Those skilled in the art will also appreciate that the term "instrument" as used and claimed herein is meant to mean any static or dynamic medical tool or device or object or any component of such a tool, device or object. The invention may be used in conjunction with any object for which the number of sterilizations needs to be counted. Moreover, while much of the disclosure is directed to surgical instruments and in particular endoscopic surgical instruments, it will be understood that the invention is not so limited, and may be used with any medical instrument. Indeed, it is the intention of the inventors that the invention have broad application since it is useful as a sterilization counter with any object which is subject to repeated sterilization. It will therefore be appreciated by those skilled in the art that yet other modifications could be made to the provided invention without deviating from its spirit and scope as so claimed.

We claim:

1. In an endoscopic surgical instrument having a proximal handle coupled to a tube containing a push rod, an integral heat responsive counter for counting the number of times the surgical instrument has been sterilized, said heat responsive counter comprising:
    a) a ring-like ratchet member having interior teeth and an exterior display surface, said ratchet member being arranged substantially coaxial to said tube, and said display surface having a plurality of incremental indicia;
    b) heat responsive advancing pawl means for engaging one of said teeth such that when said medical instrument is subjected to a sterilization temperature, said advancing pawl means moves said tooth a first distance to advance said ratchet member so that a next one of said incremental indicia is indicated;
    c) blocking pawl means for engaging said ratchet member and for allowing movement of said ratchet member in one direction only.

2. In an endoscopic surgical instrument according claim 1, said heat responsive counter further comprising:
    d) hub means located between said tube and said ratchet member, said hub means for holding a first end of at least one of said advancing pawl means, and said blocking pawl means.

3. In an endoscopic surgical instrument, according to claim 1, wherein:
    said endoscopic surgical instrument further comprises a ferrule which is substantially coaxial with said tube, said ferrule having a slot therein for housing said ratchet member of said heat responsive counter, and said ferrule includes window means for masking all but one of said indicia at a time.

4. In an endoscopic surgical instrument according to claim 3, wherein:
    said incremental indicia comprise sequential numbers.

5. In an endoscopic surgical instrument according to claim 2, wherein:
    said heat responsive advancing pawl means comprises a bimetallic member having a first end coupled to said hub means and a second end engaging said teeth.

6. In an endoscopic surgical instrument according to claim 1, wherein:
    said teeth number at least one less than said plurality of incremental indicia such that upon advancing said ratchet member to a last one of said incremental indicia said advancing pawl means no longer engages a tooth and said ratchet member can no longer be advanced by said advancing pawl means.

7. In an endoscopic surgical instrument according to claim 1, further comprising:
    d) removable locking means engaging said ratchet member to prevent movement of said ratchet member by said heat responsive advancing pawl means prior to removal of said removable locking means.

8. In an endoscopic surgical instrument according to claim 3, wherein:

said ratchet member is provided with a bore for receiving said removable locking means, and
said endoscopic surgical instrument further comprises a ferrule which is substantially coaxial with said tube, said ferrule having a slot therein for housing said ratchet member of said heat responsive counter, and said ferrule including a window means for masking all but one of said indicia at a time and a through bore for receiving said removable locking means.

9. A medical instrument, comprising:
a) a proximal handle;
b) distal manipulating means coupled to said proximal handle; and
c) an integral heat responsive counter for counting the number of times the tool has been sterilized, wherein,
said integral heat responsive counter is located in said proximal handle, and
said integral heat responsive counter comprises a use indicator having a plurality of sequential indicia, and heat responsive means for indicating a next one of said indicia when said medical instrument is sterilized.

10. A medical instrument according to claim 9, wherein:
said proximal handle has an orifice in which said integral heat responsive counter is located and a window over said orifice, and
said use indicator comprises a ring-like ratchet member having a plurality of interior teeth and an exterior display surface having said plurality of sequential indicia, said ratchet member being rotatably mounted within said orifice, said exterior display surface being visible through said window, and
said heat responsive means comprises advancing pawl means which is responsive to heat such that when heated during sterilization of said medical instrument said advancing pawl means expands a first distance, and when cooled, said advancing pawl means contracts said first distance, and said advancing pawl means engage one of said teeth when contracting or expanding and thereby advances said ratchet member.

11. A medical instrument according to claim 10, wherein:
said integral heat responsive counter further comprises a blocking pawl means for engaging said ratchet member to allow movement of said ratchet member in one direction only.

12. A medical instrument according to claim 11, wherein:
said integral heat responsive counter further comprises a hub means for coupling to said housing, said hub means being substantially centrally located relative said ratchet member, and said hub means receiving a first end of at least one of said blocking pawl means and said advancing pawl means.

13. An apparatus for counting the number of times a medical instrument has been sterilized, comprising:
a) a use indicator attached to or in the surgical instrument, said use indicator having a plurality of sequential indicia;
b) heat responsive means for indicating a next one of said indicia when the medical instrument is sterilized; and
c) actuation means for preventing said heat responsive member from indicating a next one of said indicia until after said actuation means is triggered.

14. An apparatus according to claim 13, further comprising:
d) last indicia stop means for preventing said heat responsive member from indicating a next one of said indicia beyond a predetermined last one of said indicia.

15. An apparatus according to claim 13, wherein:
said use indicator comprises a ratchet member having a plurality of teeth, and
said heat responsive member comprises an advancing pawl means for engaging one of said teeth such that when said advancing pawl means is subjected to a substantial change in temperature said advancing pawl means moves said tooth a first distance to advance said ratchet member so that a next one of said incremental indicia is indicated.

16. An apparatus according to claim 13, wherein:
said use indicator comprises a ratchet wheel having inner teeth and an outer display surface, said outer display surface containing said plurality of indicia, and
said heat responsive member comprises a bimetallic pawl engaging said teeth.

17. An apparatus according to claim 13, wherein:
said heat responsive member comprises a bimetallic element.

18. An apparatus according to claim 14, wherein:
said use indicator comprises a ratchet wheel having a plurality of teeth,
said heat responsive member comprises a pawl engaging said teeth, and
said last indicia stop means comprises a space between two adjacent teeth.

19. An apparatus according to claim 13, wherein:
said actuation means comprises a removable pin, said actuation means being triggered by removing said pin.

20. An apparatus according to claim 15, further comprising:
c) blocking pawl means for engaging said ratchet member so as to allow movement of said ratchet member in one direction only;

21. An apparatus according to claim 20, wherein:
said ratchet member is in the form of a ring.

22. An apparatus according to claim 21, wherein:
said teeth are located on an interior surface of said ring and said display surface is located on an exterior surface of said ring.

23. An apparatus according to claim 21, wherein said medical instrument has a recess, and wherein:
said apparatus is located in said recess in said medical instrument, and one of said medical instrument and said apparatus includes indicator means for identifying which of said plurality of incremental indicia is for display.

24. An apparatus according to claim 23, wherein:
said indicator means comprises a window over said recess.

25. An apparatus according to claim 21, wherein said medical instrument has a ferrule, and wherein:
said apparatus is located in said ferrule of said medical instrument, and one of said medical instrument and said apparatus includes indicator means for identifying which of said plurality of incremental indicia is for display.

26. An apparatus according to claim 20, wherein:
said advancing pawl means is a curved bimetallic member which engages a shoulder of a tooth of said ratchet member and expands at least said first distance when heated a first amount, thereby moving said ratchet member during heating, and contracts at least said first distance when cooled said first amount.

27. An apparatus according to claim 20, wherein:
said advancing pawl means is a curved bimetallic member which expands at least said first distance when heated a first amount, and engages a shoulder of a tooth of said ratchet member and contracts at least said first distance when cooled said first amount, thereby moving said ratchet member during cooling.

28. An apparatus according to claim 20, further comprising:
d) movement limiting means for limiting movement of said advancing pawl means, wherein
said advancing pawl means is a curved bimetallic member which expands when heated, and contracts when cooled, wherein said movement limiting means limits movement of said curved bimetallic member to approximately said first distance upon heating and cooling.

29. An apparatus according to claim 26, wherein:
said movement limiting means comprises a hub means for holding one end of said curved bimetallic member, said hub means having a key extending from said hub, said key engaging said curved bimetallic member to limit movement of said bimetallic member to approximately said first distance upon heating and cooling.

30. An apparatus according to claim 28, wherein:
said movement limiting means comprises a first stop means for limiting movement of said curved bimetallic member upon heating, and a second stop means for limiting movement of said curved bimetallic member upon cooling.

31. An apparatus according to claim 20, further comprising:
d) removable locking means for engaging said ratchet member and preventing movement of said ratchet member by said heat responsive advancing pawl means until removed.

32. An apparatus according to claim 31, wherein:
said removable locking means comprises a locking pin and said ratchet member includes a bore for receiving said pin.

33. An apparatus according to claim 31, wherein:
said removable locking means is coupled to packaging containing said medical instrument such that when said instrument is removed from said packaging said removable locking means is removed.

34. An apparatus according to claim 20, wherein:
said teeth number at least one less than said plurality of incremental indicia such that upon advancing said ratchet member to a last one of said incremental indicia said advancing pawl means no longer engages a tooth and said ratchet member can no longer be advanced by said advancing pawl means.

35. An apparatus according to claim 13, wherein:
said use indicator comprises a rotating member having an outer surface displaying said sequential indicia, and
said heat responsive means comprises
a stationary ratchet member and
a bimetallic pawl having a fixed end and a free end, said fixed end coupled to said use indicator, and said free end engaging said ratchet member.

36. An apparatus according to claim 13, wherein:
said use indicator comprises a rotating member having an outer surface displaying said sequential indicia, and a toothed axle, and
said heat responsive means comprises a bimetallic pawl having a fixed end and a free end, said free end engaging said toothed axle.

37. An apparatus according to claim 13, further comprising:
d) an escapement mechanism having a gear coupled to said use indicator and having an advancement mechanism coupled to said heat responsive means.

38. An apparatus according to claim 37, wherein:
said heat responsive means comprises an aneroid bellows.

39. An apparatus according to claim 37, wherein:
said heat responsive means comprises a cylinder and a piston, said cylinder containing a heat responsive medium whereby heating and cooling of said medium causes movement of said piston.

40. An apparatus according to claim 13, wherein:
said use indicator comprises a fluid conduit which receives fluid, and
said heat responsive means comprises a fluid supply with said fluid, and a heat responsive pump means, with said pump means coupled to said fluid conduit, and said fluid supply coupled to said heat responsive pump means, wherein when said apparatus is heated, said heat responsive pump means pumps said fluid into said fluid conduit, and when said apparatus is cooled said fluid supply supplies additional fluid to said heat responsive pump means.

41. An apparatus according to claim 40, wherein:
said heat responsive means further comprises first and second valve means, said first valve means coupled between said fluid supply and said heat responsive pump means for preventing fluid received by said heat responsive pump means from reentering said fluid supply, and said second valve means coupled between said heat responsive pump means and said fluid conduit for preventing fluid received by said fluid conduit from reentering said heat responsive pump means.

42. An apparatus according to claim 41, wherein:
said use indicator further comprises a plurality of containers sequentially coupled to said fluid conduit, said plurality of containers sequentially receiving fluid pumped by said heat responsive fluid pump means.

43. An apparatus according to claim 42, wherein:
said heat responsive pump means includes a measuring reservoir which holds precisely enough of said fluid such that when said heat responsive fluid pump means pumps the fluid in said measuring reservoir, an additional container is substantially filled.

44. An apparatus according to claim 13, wherein:
said use indicator comprises a strip with a zigzag slot, and
said heat responsive means comprises a bimetallic member having a fixed end and a free end, said free end engaging said zigzag slot.

45. An apparatus according to claim 44, wherein:

said use indicator further comprises a plurality of teeth, and a direction limiting pawl engaging said teeth.

46. An apparatus according to claim 13, further comprising:
   d) a power supply means, wherein
   said use indicator comprises an electronic display and an electrical circuit means for driving said display, and
   said heat responsive means comprises an electronic temperature sensor coupled to said electrical circuit means, and
   said power supply means is coupled to and powers said electronic display, said electrical circuit means, and said electronic temperature sensor means.

47. An apparatus according to claim 46, wherein:
   said electronic display comprises an LCD.

48. An apparatus according to claim 46, wherein:
   said electronic temperature sensor comprises a device selected from the group consisting of a thermistor, a diode, a transistor, and an integrated circuit.

49. An apparatus according to claim 46, wherein:
   said electrical circuit means and said electronic temperature sensor means are provided on a single circuit board.

50. An apparatus according to claim 46, wherein:
   said electrical circuit means for driving said display further comprises a microprocessor.

51. An apparatus according to claim 46, wherein:
   said power cell is a coin cell selected from the group consisting of carbon-zinc, silver oxide, and lithium-iodide.

52. An apparatus according to claim 46, further comprising:
   e) a housing containing said electronic display, said electronic temperature sensor, said electrical circuit means, and said power supply means.

53. An apparatus according to claim 52, further comprising:
   f) adhesive means on said housing for attaching said housing to said instrument.

54. An apparatus according to claim 52, wherein:
   said housing comprises a cylinder with an open face and a removable back.

55. An apparatus according to claim 46, wherein:
   said electronic display comprises an LCD,
   said electronic temperature sensor comprises a device selected from the group consisting of a thermistor, a diode, a transistor, and an integrated circuit,
   said electrical circuit means and said electronic temperature sensor means are provided on a single circuit board,
   said electrical circuit means for driving said display further comprises a microprocessor, and
   said power cell is a coin cell selected from the group consisting of carbon-zinc, silver oxide, and lithium-iodide.

* * * * *